United States Patent [19]

Broom et al.

[11] Patent Number: 4,931,434
[45] Date of Patent: Jun. 5, 1990

[54] PENEM COMPOUNDS

[75] Inventors: Nigel J. P. Broom; Gerald Brooks, both of Betchworth; Brian P. Clarke, Epsom, all of England

[73] Assignee: Beecham Group p.l.c., Brentford, England

[21] Appl. No.: 285,736

[22] Filed: Dec. 16, 1988

[30] Foreign Application Priority Data

Dec. 18, 1987 [GB] United Kingdom ................ 8729614

[51] Int. Cl.⁵ ................ C07D 499/00; A61K 31/425
[52] U.S. Cl. .................................. 514/192; 514/195; 540/310
[58] Field of Search ................ 540/310; 514/192, 193

[56] References Cited

U.S. PATENT DOCUMENTS 4,798,828 1/1989 Osbourne ........................... 514/192

Primary Examiner—Nicholas S. Rizzo
Attorney, Agent, or Firm—Hopgood, Calimafde, Kalil, Blaustein & Judlowe

[57] ABSTRACT

Compounds of the general formula (II):

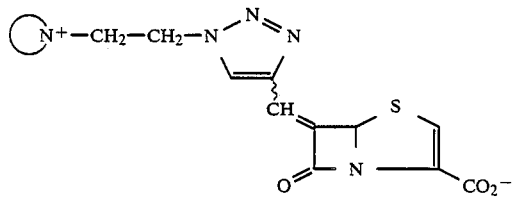

in which
$N^+$ denotes an unsubstituted or substituted nitrogen-containing heterocyclyl ring bonded to the remainder of the molecule through a ring nitrogen atom and carrying a positive charge on said nitrogen atom;
and the wavy line denotes either the E- or Z-isomeric position,
are novel and are useful in the treatment of antibacterial infection in humans or animals.

9 Claims, No Drawings

PENEM COMPOUNDS

This invention relates to novel β-lactam compounds and in particular to novel 6-(substituted methylene) penems which have β-lactamase inhibitory and antibacterial properties. The compounds are therefore useful in the treatment of antibacterial infections in humans or animals, either alone or in combination with other antibiotics.

European Patent Publication No. EP 0 154 132 A (Beecham; published 11 September 1985) (the contents of which is incorporated herein by reference thereto) describes compounds of the general formula I, which exhibit β-lactamase inhibitory action and synergistic activity:

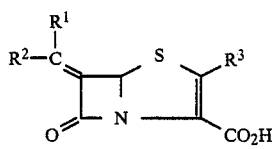

and their pharmaceutically acceptable salts and in-vivo hydrolysable esters, in which one of $R^1$ and $R^2$ denotes hydrogen, the other of $R^1$ and $R^2$ denotes an unsubstituted or substituted five-membered hetero-aromatic ring bonded through a carbon atom thereof and having one hetero-atom selected from nitrogen, oxygen and sulphur and additionally having from one to three nitrogen atoms, and $R^3$ denotes hydrogen or an organic group.

Such compounds are advantageously in the form of the 5R-isomer, that is to say in the form of structure IA:

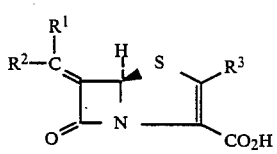

Among the compounds described in EP 0 154 132 A are compounds of the general formula I in which $R^1$ or $R^2$, preferably $R^1$, denotes a triazolyl group, especially a 1-substituted-1,2,3-triazol-4-yl group, and the other of $R^1$ and $R^2$ denotes hydrogen. More specifically, the said publication describes the compound of the general formula IA in which $R^1$ denotes a 1-methyl-1,2,3-triazol-4-yl group and each of $R^2$ and $R^3$ denotes hydrogen, namely:

(5R) (Z)-6-(1-methyl-1,2,3-triazol-4-yl-methylene) penem-3-carboxylic acid;

as well as its pharmaceutically acceptable salts and in-vivo hydrolysable esters.

Further crystalline and hydrated forms of that compound and its salts are described in European Patent Publication No. EP 0 210 814 A (Beecham; published 04 Feb. 1987) (the contents of which is incorporated herein by reference thereto).

Further details of suitable esters and salts of compounds of the general formula I, and also details of methods of preparing the compounds and the manner of formulating them into pharmaceutical compositions and using them for therapeutic treatment, are given in No. EP 0 154 132 A.

Improved methods of preparing the compounds of the general formula I are described in European Patent Publication No. EP 0 232 966 A (Beecham; published 19 Aug. 1987) (the contents of which is incorporated herein by reference thereto).

It has now been found that certain 6-(1-substituted 1,2,3-triazol-4-yl-methylene)penems exhibit improved activity as compared with the previously described compounds.

Accordingly, the present invention provides a compound of the general formula II

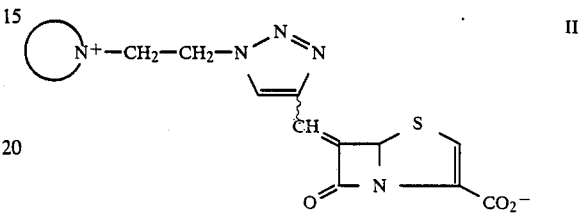

in which

denotes an unsubstituted or substituted nitrogen-containing heterocyclyl group bonded to the remainder of the molecule through a ring nitrogen atom and carrying a positive charge on said nitrogen atom;

and the wavy line denotes either the E- or Z-isomeric position.

The nitrogen-containing heterocylyl group may be monocyclic or bicyclic. In the case of a bicyclic group, the second ring may be a heterocyclic ring or a carbocyclic ring.

The nitrogen-containing heterocyclyl group may suitably contain up to 6, more usually 5 or 6, ring atoms in the or each ring, with up to four hetero-atoms in the or each ring selected from oxygen, nitrogen and sulphur, there being at least one ring nitrogen atom.

The nitrogen-containing heterocyclyl group is suitably an aromatic group, and is advantageously an unsubstituted or substituted pyrid-1-yl group.

Examples of suitable optional substituents for the nitrogen-containing heterocyclyl group include unsubstituted or substituted $(C_{1-6})$alkyl, $(C_{2-6})$alkenyl, $(C_{2-6})$alkynyl, $(C_{3-7})$cycloalkyl, and $(C_{3-7})$cycloalkyl$(C_{1-6})$alkyl groups, as well as aryl, aryl$(C_{1-6})$alkyl, $(C_{1-6})$alkanoyl, $(C_{1-6})$alkanoyloxy, heterocyclyl, amino, $(C_{1-6})$alkanoylamino, (mono or di)-$(C_{1-6})$alkylamino, hydroxy, $(C_{l-6})$alkylsulphinyl, $(C_{1-6})$alkylsulphonyl, heterocyclylthio, arylthio, sulphamoyl, carbamoyl, amidino, guanidino, nitro, halogen, carboxy esters, arylcarbonyl and heterocyclylcarbonyl groups. Examples of suitable substituents for the alkyl and other groups in the first part of the above list are those groups listed in the second part of the above list. Further suitable substituents for the nitrogen-containing heterocyclyl group include divalent substituents forming, with the heterocyclyl ring, a bicyclic ring system, for example $(C_{1-6})$alkylene and $(C_{2-6})$alkenylene.

The term 'heterocyclyl' as used herein in the above list of substituents includes aromatic and non-aromatic, single and fused, rings containing up to four heteroatoms in each ring selected from oxygen, nitrogen and sulphur, which rings may be unsubstituted or substituted by up to three groups selected from halogen, $(C_{1-6})$alkyl, $(C_{1-6})$alkoxy, halo$(C_{1-6})$alkyl, hydroxy, amino, carboxy, $(C_{1-6})$alkoxycarbonyl, $(C_{1-6})$alkoxycarbonyl$(C_{1-6})$alkyl, aryl, $(C_{1-6})$alkylthio, arylthio, mercapto and oxo groups.

The term 'aryl' as used herein includes phenyl and naphthyl, which may be unsubstituted or substituted by up to five, preferably up to three, groups selected from halogen, $(C_{1-6})$alkyl, phenyl, $(C_{1-6})$alkoxy, halo$(C_{1-6})$alkyl, hydroxy, amino, nitro, carboxy, $(C_{1-6})$alkoxycarbonyl,$(C_{1-6})$alkoxycarbonyl$(C_{1-6})$alkyl, $(C_{1-6})$alkylcarbonyloxy, $(C_{1-6})$alkylcarbonyl $(C_{1-6})$alkylthio, arylthio, and mercapto groups.

The compounds of the general formula II constitute internal salts with a positive charge on the nitrogen atom of the heterocyclyl ring and a negative charge on the 3-carboxy group of the penem ring system.

The compounds of the general formula II may exist in two optically active forms and it is to be understood that both such forms as well as racemic mixtures thereof are embraced by the present invention. It is believed that the more active form is that of structure IIA:

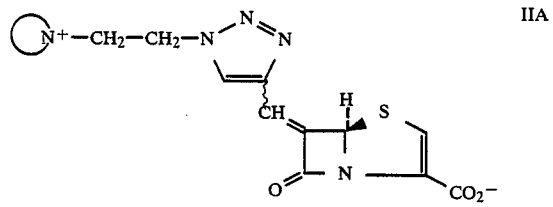   IIA in which

is defined as above. in which

Moreover, the compounds of the general formula II may exist in two isomeric forms at the methylene group, that is to say at the 8-position, namely the E- and Z-isomeric forms. The Z-isomer is preferred as generally being the more active form.

Examples of individual compounds according to the invention include:
(5R)-(Z)-6-[1-(2-pyridinioethyl)-1,2,3-triazol-4-ylmethylene]penem-3-carboxylate;
(5R)-(Z)-6-(1-[2-(3-ethylpyridinio)ethyl]-1,2,3-triazol-4-ylmethylene)penem-3-carboxylate;
(5R)-(Z)-6-(1-[2-(4-methylpyridinio)ethyl]-1,2,3-triazol-4-ylmethylene)penem-3-carboxylate;
(5R)-(Z)-6-(1-[2-(2-methylpyridinio)ethyl]-1,2,3-triazol-4-ylmethylene)penem-3-carboxylate;
(5R)-(Z)-6-(1-[2-(4-cyclopropylpyridinio)ethyl]-1,2,3-triazol-4-ylmethylene)penem-3-carboxylate;
(5R)-(Z)-6-(1-[2-(2,3-cyclopentenopyridinio)ethyl]-1,2,3-triazol-4-ylmethylene)penem-3-carboxylate;
(5R)-(Z)-6-(1-[2-(4-phenylpyridinio)ethyl]-1,2,3-triazol-4-ylmethylene)penem-3-carboxylate;
(5R)-(Z)-6-(1-[2-(3-hydroxymethylpyridinio)ethyl]-1,2,3-triazol-4-ylmethylene)penem-3-carboxylate; and
(5R)-(Z)-6-[1-(2-pyridinioethyl)-1,2,3-triazol-4-ylmethylene]penem-3-carboxylate hemihydrate.

The compounds according to the invention are advantageously provided in crystalline form, which will in some cases also be in hydrated form.

A compound of the general formula II given above, may be prepared by the reaction of a compound of the formula

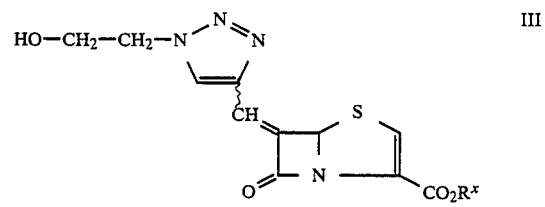   III in which $R^x$ denotes a carboxy-protecting group,
with trifluoromethanesulphonic anhydride and a base, and simultaneously or subsequently with a compound of the general formula

   IV namely an unsubstituted or substituted nitrogen-containing heterocyclyl compound,
followed by removal of the carboxy-protecting group $R^x$.

In many cases, the heterocyclyl compound of the formula IV will be sufficiently basic to serve as the base (e.g. pyridine), whereas in other cases it may be advantageous to include a separate base in the reaction (e.g. 2,6-lutidine).

Suitable carboxy-protecting groups $R^x$ are those given in EP No. 0 232 966A. It has been found that p-methoxybenzyl is particularly suitable for use as the carboxy-protecting group, in which case its removal may suitably be effected by treatment with aluminium trichloride and anisole.

The reaction with the trifluoromethanesulphonic anhydride and, when used, the treatment with the aluminium trichloride/anisole are both suitable carried out at a low temperature, advantageously from $-60°$ C. to $-20°$ C., suitably about $-40°$ C. The reaction with the nitrogen-containing heterocyclyl compound is suitably carried out at from $-10°$ C. to $+30°$ C., preferably about $0°$ C.

Removal of the carboxy-protecting group $R^x$ generates the desired internal salt.

A compound of the formula III given above may be prepared using the methods described in the above-mentioned EP No. 0 232 966 A. In particular, such compounds may be prepared using the procedure described as 'Route F' in that publication in which $R^{12}$ denotes the moiety

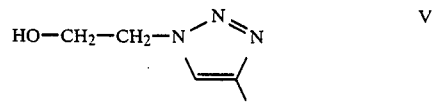   V in which the hydroxy group may optionally be protected.

Thus, a 6-halopenem may be reacted with an aldehyde of the formula

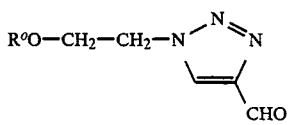

VI in which R⁰ denotes a hydroxy-protecting group.

Examples of suitable hydroxy protecting groups R⁰ include trityl (triphenylmethyl), dimethoxytrityl (4,4'-dimethoxy-triphenylmethyl), trimethoxytrityl (4,4',4''-trimethoxy-triphenyl-methyl), trimethylsilyl, t-butyl-dimethylsilyl, t-butyldiphenylsilyl, benzyloxycarbonyl, p-methoxybenzyloxycarbonyl, 2-(trimethylsilyl)ethoxycarbonyl, acetonyloxycarbonyl, and allyloxycarbonyl groups. An aldehyde of the general formula VI may, for example, conveniently be prepared from an alkyl 1-(2-hydroxyethyl)-1,2,3-triazole-4-carboxylate (prepared according to the method of S. M. Spojanovic, *Collect, Czeck. Chem. Comm.*, 1967, 32. 2155), first by introduction of the hydroxy-protecting group in a conventional manner, for example by reaction with di- or tri-methoxytrityl chloride, followed by reduction of the carboxylate group to a primary alcohol group, and then oxidation to the desired aldehyde function.

Following reaction of the aldehyde of the formula VI with the 6-halopenem, and subsequent reductive elimination of the halohydrin thus formed, to give a 6-methylene-penem, as described in EP No. 0 232 966 A, the hydroxy protecting group may be removed in a conventional manner, for example by acidic hydrolysis, to give the desired compound of the formula IV.

As indicated previously, the compounds according to the invention have β-lactamase inhibitory activity and are useful in the treatment of bacterial infections.

Accordingly, the present invention also provides a method of treating bacterial infection which comprises administering to a human or animal in need thereof an antibacterially effective amount or a β-lactamase inhibitory amount of compound of general formula II.

Advantageously, said compound is administered to said human or animal in conjunction with the prior, simultaneous or subsequent administration of a penicillin, cephalosporin, or other β-lactam antibiotic.

Details of administering the compound according to the invention are given in EP No. 0 154 132A.

Accordingly, according to a further aspect, the present invention provides a pharmaceutical composition comprising a compound according to the invention in admixture or conjunction with a pharmaceutically acceptable carrier. The composition may also comprise a penicillin, cephalosporin or other β-lactam antibiotic.

Details of formulating such compositions and using the compound according to the invention are given in EP No. 0 154 132 A.

The following Preparations 1-6 and the following Scheme 1 illustrate the preparation of a compound of the formula IV, and Examples 1-9 and Scheme 2 illustrate the preparation therefrom of compounds according to the present invention.

In the preparations and examples, all temperatures quoted are in °C.

In the formulae in Schemes 1 and 2:
DMT denotes 4,4'-dimethoxytrityl, and
pMB denotes p-methoxybenzyl.

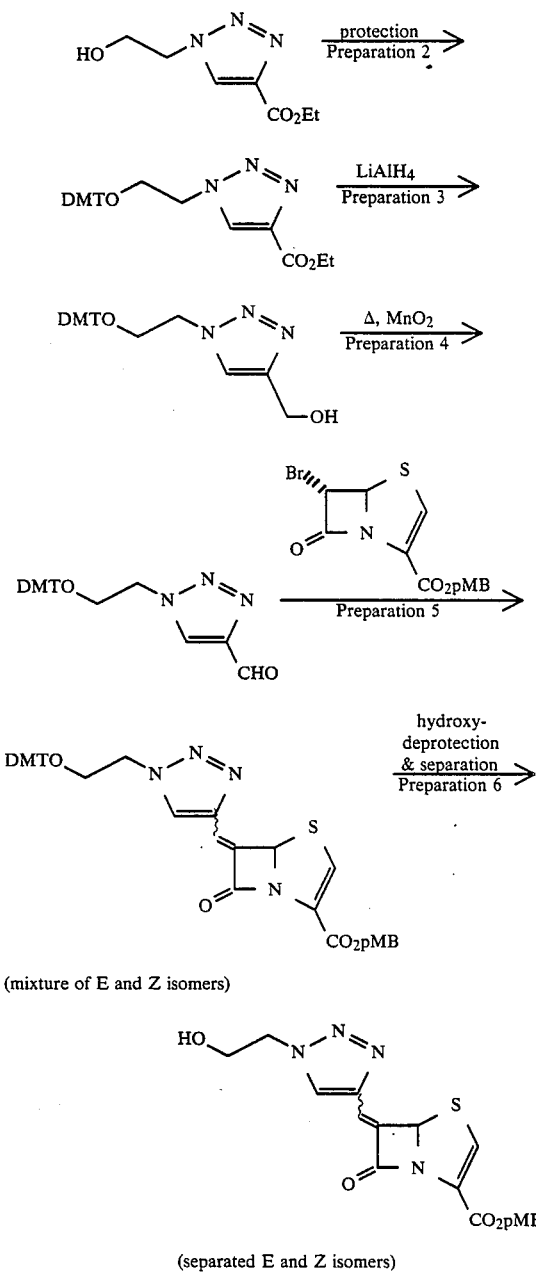

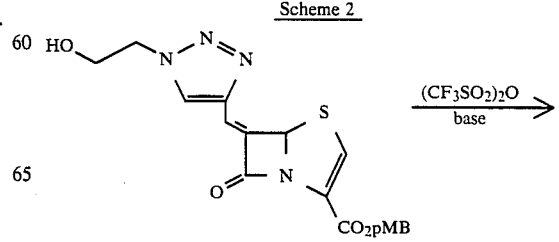

-continued
Scheme 2

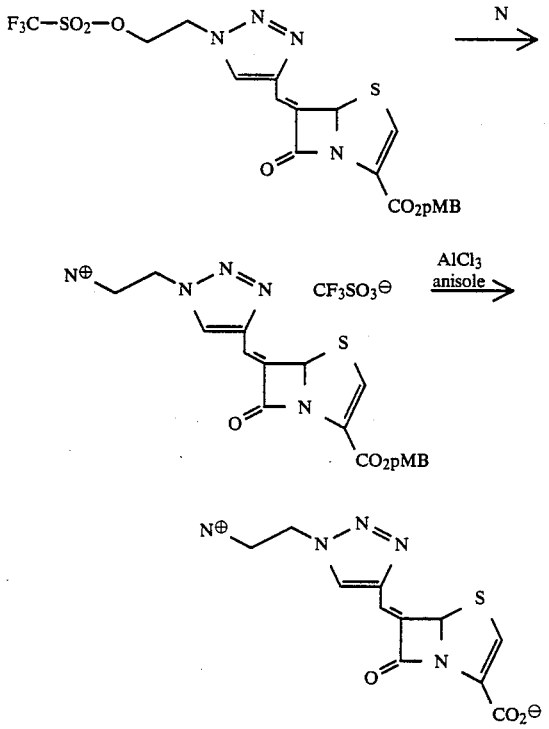

PREPARATION 1

Ethyl 1-(2-Hydroxyethyl)-1,2,3-triazole-4-carboxylate

A solution of ethanolamine (60 ml, 1 mole) in methanol (320 ml) at 5° was treated with formic acid until a pH of 5 was obtained. A solution of ethyl α-formyldiazoacetate (crude, approximately 0.3 mole) in methanol (320 ml) was then added and the mixture stirred at room temperature for two days. The mixture was then evaporated, chloroform (1 liter), then water (200 ml) was added and the mixture was treated with sodium bicarbonate until a pH of 7 was reached. The phases were separated and the aqueous phase saturated with sodium chloride and extracted with chloroform (6 x 300 ml). The combined organic phases were dried (MgSO$_4$), filtered and evaporated. The residue was then dissolved in toluene (approximately 100 ml). The resulting crystalline solid was filtered, washed with ether and dried to provide the title compound (41.6 g) as a solid; $\lambda_{max}$ (nujol) 3320, 3140, 1725 cm$^{-1}$; δ (CDCl$_3$), 1.38 (3H, t, J 7.5Hz), 4.00–4.80 (7H, m, becomes 6H, m on D$_2$O exch), 8.40 (1H, s). This material was pure enough for further synthetic progression.

PREPARATION 2

Ethyl 1-[2-(4,4'-Dimethoxytrityloxy)ethyl]11-1,2,3-triazole-4-carboxylate

A solution of the product from Preparation 1 (20.3 g) in dry dichloromethane (200 ml) at 5° was sequentially treated with triethylamine (15.4 ml) and 4,4'-dimethoxytrityl chloride (37.4 g). The reaction mixture was warmed to room temperature and, after 1 hour, ethyl acetate (800 ml) was added. The mixture was washed with 0.2 N HCl, brine, then dried (MgSO$_4$) and evaporated. The residue was chromatographed on silica eluting with ethyl acetate/hexane mixtures to provide the title compound as an amorphous solid (41.2 g); $\lambda_{max}$ (CHCl$_3$) 1725 cm$^{-1}$; δ(CDCl$_3$), 1.40 (3H, t, J 6.5 Hz), 3.44–3.80 (m) overlaying 3.68 (s) (together 8H), 4.35–4.69 (4H, m), 6.82 (4H, d, J 9.0 Hz), 7.25 (4H, d, J 9.0 Hz), 7.30 (5H, s), 8.22 (1H, s).

PREPARATION 3

1-[2-(4,4'-Dimethoxytrityloxy)ethyl]-4-hydroxymethyl-1,2,3-triazole

A solution of the product from Preparation 2 (40 g) in tetrahydrofuran (400 ml) at 5° under argon was treated with lithium aluminium hydride (4.67 g). After 30 minutes the cooling bath was removed and after a further hour water (175 ml) was carefully added. The resulting gel was treated with ethyl acetate (2 liters) and filtered. The filtrate was washed with water and brine, then dried and evaporated. The residue was chromatographed on silica eluting with ethyl acetate/hexane mixtures to give the title compound (34.5 g) as an amorphous solid; δ(CDCl$_3$) 2.93 (1H, bs), 3.30–3.55 (2H, m), 3.77 (6H, s), 4.30–4.60 (2H, m), 4.81 (2H, s), 6.83 (4H, d, J 9.0 Hz), 7.23 (4H, d, J 9.0 Hz), 7.27 (5H, bs), 7.67 (1H, s).

PREPARATION 4

1-[2-(4,4'-Dimethoxytrityloxy)ethyl]-1,2,3-triazole-4-carboxaldehyde

A solution of the product from Preparation 3 (34.5 g) in benzene (600 ml) was treated with manganese dioxide (48.3 g) and the mixture was refluxed with provision for the azeotropic removal of water (Dean and Stark apparatus containing 4A molecular sieves) for 18 hours. The reaction mixture was diluted with dichloromethane (1.5 liters) and filtered through Kieselguhr, washing the pad well with dichloromethane. The filtrate was evaporated and chromatographed on silica eluting with ethyl acetate/hexane mixtures to give the title compound (27 g) as an amorphous solid. $\lambda_{max}$ (CHCl$_3$) 1705cm$^{-1}$; δ(CDCl$_3$), 3.60 (2H, t, J 4.5 Hz), 3.76 (6H, s), 4.50 (2H, t, J 4.5 Hz), 6.81 (4H, d, J 8.5 Hz), 7.22 (4H, d, J 8.5 Hz), 7.29 (5H, s), 8.21 (1H, s), 10.15 (1H, s).

PREPARATION 5

(5R) p-Methoxybenzyl 6-(1-[2-(4,4'-Dimethoxytrityloxy)ethyl]-1,2,3-triazole-4-ylmethylene)penem-3-carboxylate A solution of diphenylamine (6.03 g) in dry tetrahydrofuran (THF) (150 ml) at −10° under argon was treated with a solution of n-butyl lithium (1.5 M, 21.8 ml) in hexane. After 10 minutes the reaction mixture was cooled to −78° and sequentially treated with a solution of (5R,6S) p-methoxybenzyl 6-bromo-penem-3-carboxylate (11.35 g) (EP No. 0 232 966 A) in THF (50 ml), then a solution of the product from Preparation 4 (13.5 g) in THF (50 ml) and finally acetic anhydride (9.61 ml). The cooling bath was removed and the reaction mixture was allowed to reach room temperature. The reaction mixture was then diluted with ethyl acetate (1 liter), washed with saturated sodium bicarbonate solution, and brine, then dried (MgSO$_4$) and evaporated.

The residue was dissolved in dimethylformamide (200 ml) and treated with ammonium chloride (4.6 g), N,N,N',N'-tetramethylethylenediamine dihydrochloride (4.09 g) and zinc powder (5.32 g), and then vigorously stirred for 1 hour. The reaction mixture was then diluted with ethyl acetate (1.5 liters) washed with 0.2N HCl (1 liter), water (1 liter), saturated sodium bicarbonate solution (500 ml) and brine (500 ml), then dried (MgSO$_4$) and evaporated. The residue was chromatographed on silica eluting with ethyl acetate/hexane mixtures to give a 1:5 mixture of E and Z isomers of the title compound as a yellow amorphous solid (13.75 g); $\gamma$max (CHCl$_3$) 1780, 1710, 1615cm$^{-1}$; $\delta$(CDCl$_3$) inter alia 6.43 (1/$_5$H, s, C5-H; E isomer), 6.63 (4/$_5$H, d, J 0.8 Hz, C5-H; Z isomer), 7.81 (4/$_5$H, s, C540-H; Z isomer), 8.92 (1/$_5$H, s, C5'-H; E isomer).

PREPARATION 6 p-Methoxybenzyl (5R)-(Z)-6-[1-(2-Hydroxyethyl)-1,2,3-triazol-4-ylmethylene)penem-3-carboxylate A solution of the mixture of products from Preparation 6 (13.75 g) in dichloromethane (1 liter) at 5° C. under argon was treated with formic acid (27.5 ml). After 1 hour water (300 mg) was added, followed by a solution of sodium hydroxide (27.5 g) in water (50 ml). The pH of the aqueous layer was adjusted to pH 9 by the addition of more sodium hydroxide solution. The organic phase was separated, washed with water (200 ml), brine (200 ml), then dried (MgSO$_4$) and evaporated. On standing the residue was observed to crystallise; ethyl acetate (100 ml) was added and the mixture warmed. The resulting cyrstalline solid (1.89 g) was collected by filtration and dried. This material was identified as the Z-isomer of the title compound; mp 137°-140° (yellow needles from ethyl acetate); [$\alpha$]D$^{20}$+420° (c 0.5 in DMSO); $\lambda_{max}$ (2% CHCl$_3$/EtOH), 288 nm ($\epsilon_m$ 25,100); $\lambda_{max}$ (nujol) 3500, 1780, 1695cm$^{-1}$; $\delta$(d$_6$-DMSO), 3.70-3.85 (m) overlaying 3.76 (s) (together 5H), 4.47 (2H, t, J 5.2 Hz), 5.09 (1H, t, J 5.2 Hz), 5.16 (2H, s), 6.67 (1H, d, J 0.8 Hz), 6.94 (2H, d, J 8.6 Hz), 7.35 (s) overlaying 7.37 (d, J 8.3 Hz) (together 3H), 7.73 (1H, s), 8.42 (1H, s). (Found C, 55.1; H, 4.3; N, 13.7; S, 7.7. C$_{19}$H$_{18}$N$_4$O$_5$S requires C, 55.1; H, 4.4; N, 13.5; S, 7.7%).

The mother liquors were concentrated and chromatographed on silica eluting with ethyl acetate/hexane mixtures to give a mixture of E- and Z-isomers of the title compound. A further quantity (0.86 g) of the Z-isomer was obtained by careful crystallisation of this mixture from ethyl acetate/hexane. Continued elution of the column gave the Z-isomer of the title compound (1.19 g).

EXAMPLE 1

(5R)-(Z)-6-[1-(2-Pyridinioethyl)-1,2,3-triazol-4-ylmethylene]penem-3-carboxylate A solution of p-methoxybenzyl (5R)-(Z)-6-[1-(2-hydroxy- ethyl)-1,2,3-triazol-4-ylmethylene]penem-3-carboxylate (1 g) and pyridine (5 ml) in dichloromethane (100 ml) was cooled to −40° C. and treated with trifluoromethanesulphonic anhydride (1.6 ml). The solution was warmed to 0° C. and stirred for 1 hour at ice-bath temperature, diluted to 1 liter with dichloromethane and washed with 2% aqueous citric acid (1 liter) and water (1 liter). The solution was dried over anhydrous magnesium sulphate and evaporated under reduced pressure to 80 ml.

A solution of anhydrous aluminium trichloride (1 g) in anisole (16 ml)/dichloromethane (4 ml) was cooled to −40° C. under argon and treated over 5 minutes with the above dichloromethane solution. The mixture was stirred at −40° C. for 15 minutes, treated with 0.5 M disodium hydrogen phosphate solution (100 ml) and allowed to warm to room temperature while stirring vigorously. The suspension was filtered through celite, washing through with water until the filtrate became colourless. The layers of the filtrate were separated and the aqueous washed with dichloromethane (50 m) and ether (50 ml) and evaporated to 20 ml. This solution was added to a column of HP20SS and the polar materials washed through with water. The required penem was eluted off with 5% acetone/water and the solutions containing penem were combined and evaporated to 50 ml then freeze-dried. The title compound was thus obtained as a yellow solid (220 mg): [$\alpha$]D$^{20}$+297° (c. 0.35; H$_2$O); 65 umax (KBr) 1758, 1688, 1638, 1601, 1579, 1551 and 1358cm$^{-1}$; $\lambda_{max}$ (H$_2$O) 266 (s) ($\epsilon$22180), 277 ($\epsilon$23360) and 371 nm ($\epsilon$1880); $\delta$(D$_2$O, with HOD at 4.80 $\delta$) 5.1-5.3 (4H, m), 6.52 (1H, S), 7.00 (1H, s), 7.13 (1H, s), 8.03 (2H, t, J 7 Hz), 8.22 (1H, s), 8.59 (1H, t, J 7 Hz), 8.68 (2H, d, J 7 Hz).

EXAMPLE 2

(5R)-(Z)-6-(1-[2-(3-Ethylpyridinio)ethyl]-1,2,3-triazol-4-ylmethylene)penem-3-carboxylate The title compound was prepared analogously to the product of Example 1, and was obtained as a yellow solid (53%): $\gamma$max (KBr) 1763, 1689, 1596, 1550 and 1370cm$^{-1}$; $\delta$(D$_2$O, with HOD at 4.80 $\delta$) 1.14 (3H, t, J 7.5 Hz), 2.75 (2H, q, J 7.5 Hz), 5.11 (4H, s), 6.52 (1H, s), 7.00 (1H, s), 7.13 (1H, s), 7.94 (1H, dd, J 8 and 6 Hz), 8.19 (1H, s), 8.30 (1H, s), 8.42 (1H, d, J 8 Hz), 8.55 (1H, d, J 6 Hz).

EXAMPLE 3

(5R)-(Z)-6-(1-2-(4-Methylpyridinio)ethyl]-1,2,3-triazol-4-ylmethylene)penem-3-carboxylate The title compound was prepared analogously to the product of Example 1, and was obtained as a yellow solid (34%): [$\alpha$]D$^{24}$+264° (c. 0.4; H$_2$O); $\lambda_{max}$ (KBr) 1763, 1684, 1640, 1597, 1550 and 1375 cm$^{-1}$; $\lambda_{max}$(H$_2$O) 264 ($\epsilon$) ($\epsilon$16800), 277 ($\epsilon$18920), and 371 nm ($\epsilon$1430); $\delta$(D$_2$O with HOD at 4.80 $\delta$), 2.62 (3H, s), 5.08 (4H, broad s), 6.50 (1H, s), 6.98 (1H, s), 7.11 (1H, s), 7.81 (2H, d, J 6 Hz), 8.20 (1H, s), 8.42 (2H, d, J 6 Hz).

EXAMPLE 4

(5R)-(Z)-6-(1-[2-(2-Methyloyridinio)ethyl]-1,2,3-triazol-4-vlmethvlene)penem-3-carboxylate The title compound was prepared analogously to the product of Example 1, and was obtained as a yellow solid (32%): [$\alpha$]D$^{23}$+322° (c. 0.5; H$_2$O); $\lambda_{max}$ (KBr) 1762, 1684, 1629, 1596, 1550 and 1377cm$^{-1}$; $\lambda_{max}$(H$_2$O) 274 ($\epsilon$24050) and 371 nm ($\epsilon$1662); $\delta$(D$_2$O with HOD at 4.80 $\delta$) 2.72 (3H, s), 5.14 (4H, s), 6.52 (1H, s), 6.99 (1H, s), 7.13 (1H, s), 7.77 (1H, t, J 7 Hz), 7.95 (1H, d, J 7 Hz), 8.24 (1H, s), 8.35 (1H, d, J 7 Hz), 8.42 (1H, t, J 7 Hz).

EXAMPLE 5

(5R)-(Z)-6-(1-[2-(4-Cyclopropylpyridinio)ethyl]-1,2,3-triazol-4-ylmethylene)penem-3-carboxylate The title compound was prepared analogously to the product of Example 1, and was obtained as a yellow solid (61%): [$\alpha$]D$^{21}$+309° (c. 0.1; H$_2$O); $\lambda_{max}$ (KBr) 1781, 1685, 1638, 1569, 1544 and 1378cm$^{-1}$; $\lambda_{max}$(H$_2$O) 262 ($\epsilon$23000), and 370 nm ($\epsilon$1245); $\delta$(D$_2$O with HOD at 4.80 δ) 1.0–1.2 (2H, m), 1.4–1.6 (2H, m), 2.1–2.3 (1H, m), 4.9–5.2 (4H, m), 6.57 (1H, s), 7.06 (1H, s), 7.18 (1H, s), 7.59 (2H d, J 7Hz), 8.18 (1H, s), 8.28 (2H, d, J 7 Hz).

EXAMPLE 6

(5R)-(Z)-6-(1-[2-(2,3-Cyclopentenopyridinio)ethyl]-1,2,3-triazol-4-ylmethylene)penem-3-carboxylate The title compound was prepared analogously to the product of Example 1, using 2,3-cyclopentenopyridine in place of pyridine, and was obtained as a yellow solid (60%): [α]D²⁰+310° (c. 0.7; H₂O); λ$_{max}$ (KBr) 1763, 1684, 1595, 1550 and 1369cm⁻¹; λ$_{max}$ (H₂O) 278 (ε27880) and 372 nm (ε1520); δ(D₂O with HOD at 4.80 δ) 2.14 (2H, quintet, J 7.5 Hz), 2.7–3.1 (2H, m), 3.11 (2H, t, J 7.5 Hz), 4.9–5.2 (4H, m), 6.47 (1H, s), 6.94 (1H, s), 7.09 (1H, s), 7.70 (1H, t, J 7 Hz), 8.21 (1H, s), 8.28 (2H, d, J 7 Hz).

EXAMPLE 7

(5R)-(Z)-6-(1-[2-(4-Phenylopyridinio)ethyl]-1,2,3-triazol-4-ylmethylene)penem-3-carboxylate A solution of p-methoxybenzyl (5R)-(Z)-6-[1-(2-hydroxy- ethyl)-1,2,3-triazol-4-ylmethylene]penem-3-carboxylate (100 mg), 2,6-lutidine (0.116 ml) and 4-phenylpyridine (775 mg) in dichloromethane (10 ml) was cooled to −40° C. and treated with trifluoromethanesulphonic anhydride (0.168 ml). The solution was warmed to 0° C. and stirred for 1 hour at ice-bath temperature, diluted to 50 ml with dichloromethane and washed with 0.5N hydrochloric acid (50 ml) and water (50 ml). The solution was dried over anhydrous magnesium sulphate and evaporated under reduced pressure to 2 ml.

A solution of anhydrous aluminium trichloride (120 mg) in anisole (3.2 ml)/dichloromethane (0.8 ml) was cooled to −40° C. under argon and treated over 1 minute with the above dichloromethane solution. The mixture was stirred at −40° C. for 10 minutes, treated with 0.5 M disodium hydrogen phosphate (11 ml) and allowed to warm to room temperature while stirring vigorously. The suspension was filtered through celite, washing through with water (100 ml) and 1:1 glacial acetic acid/water (100 ml). The layers of the filtrate were separated and the aqueous washed with dichloromethane (100 ml) and ether (100 ml) and filtered through a glass fiber pad. The aqueous acetic acid solution was evaporated under reduced pressure to about 2 ml and the resulting yellow solid was filtered off, washed with water and acetone and then dried under vacuum over P₂O₅, giving the title compound (96 mg): [α]D¹⁹+211° (c. 0.4; H₂O/CH₃COOH 1:1); λ$_{max}$(KBr) 1775, 1690, 1636, 1599, 1544 and 1364cm⁻¹; λ$_{max}$ (H₂O/CH₃COOH 1:1) 288 nm (ε20470); δ (D₂O/CD₃COOD 1:1 with acetone at 2.2 δ) 5.25 (4H, broad s), 6.60 (1H, s), 7.24 (1H, s), 7.50 (1H, s), 7.6–7.7 (3H, m), 7.9–8.0 (2H, m), 8.3–8.4 (3H, m), 8.76 (2H, d, J 7 Hz).

EXAMPLE 8

(5R)-(Z)-6-(1-[2-(3-Hydroxymethylpyridinio)ethyl]-1,2,3-triazol-4-ylmethylene)penem-3-carboxylate .

A solution of p-methoxybenzyl (5R)-(Z)-6-[1-(2-hydroxyethyl)-1,2,3-triazol-4-ylmethylene]penem-3-carboxylate (50 mg) and 2,6-lutidine (0.06 ml) in dichloromethane (6 ml) was cooled to −40° C. and treated with trifluoromethanesulphonic anhydride (0.06 ml). After 5 minutes 3-pyridylcarbinol (0.12 mg) was added and the reaction mixture allowed to warm to 0° C. A procedure analogous to that of Example 1 was then followed, to provide the title compound as a yellow solid (3.3 mg): γ$_{max}$ (KBr) 1762, 1598, 1551 and 1383cm⁻¹; δ(D₂O with HOD at 4.80 δ) 5.15 (6H, broad s), 6.54 (1H, s), 7.01 (1H, s), 7.14 (1H, s), 7.98 (1H, dd, J 8 and 6 Hz) 8.21 (1H, s), 8.4–8.7 (3H, m).

EXAMPLE 9

(5R)-(Z)-6-[1-(2-Pyridinioethyl)-1,2,3-triazol-4vlmethvlene]penem-3-carboxylate hemihydrate A solution of the product from Example 1 (130 mg) was dissolved in water (0.65 ml) and the solution left to crystallise at 5°. After 3 hours the crystalline solid was removed by filtration, washed with acetone (1 ml), ether (2 ml) then dried to provide the title compound (54 mg) as yellow needles; [α]D²⁰ (c=1 in H₂O) +397.8°; λ$_{max}$ (H₂O) 266 nm (ε24400), 279 (25580), 372 (2120); λ$_{max}$ (KBr) 3423, 1757, 1688, 1637 1601cm⁻¹; δ(D₂O) 5.08–5.25 (4H, m), 6.51 (1H, s). 6.98 (1H, s), 7.12 (1H, s), 8.02 (2H, dd, J 6.8, 7.9 Hz), 8.20 (1H, s), 8.57 (1H, dt, J 1.3, 7.9 Hz), 8.65 (2H, dd, J 1.3, 6.8 Hz). (Found: C, 52.8; H, 3.7; N, 18.9; S, 8.8. C₁₆H₁₃N₅O₃S. ½H₂O requires C, 52.8; H, 3.9; N, 19.2; S, 8.8%).

We claim:

1. A compound represented by the formula (II):

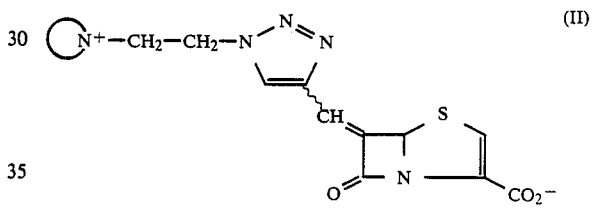

in which

denotes an unsubstituted or substituted nitrogen-containing heterocyclyl group bonded to the remainder of the molecule through a ring nitrogen atom and carrying a positive charge on said nitrogen atom, said nitrogen-containing heterocyclyl group being monocyclic or bicyclic and having up to six ring atoms in the or each ring with up to four hetero-atoms in the or each ring selected from oxygen, nitrogen and sulfur, there being at least one ring nitrogen, wherein the substitutents for the nitrogen containing heterocyclyl group are selected from one or more of the following groups; unsubstituted or substituted (C₁₋₆)alkyl, (C₂₋₆)alkenyl, (C₂₋₆)alkynyl, (C₃₋₇)cycloalkyl, and (C₃₋₇)cycloalkyl(C₁₋₆)alkyl groups, as well as aryl, aryl(C₋₆)alkyl, (C₁₋₆)alkanoyl, (C₁₋₆)alkanoyloxy, heterocyclyl, amino, (C₁₋₆)alkanoylamino, (mono or di)-(C₁₋₆)alkylamino, hydroxy, (C₁₋₆)alkylsulphinyl, (C₁₋₆)alkylsulphonyl, heterocyclylthio, arylthio, sulphamoyl, carbamoyl, amidino, guanidino, nitro, halogen, carboxy esters, arylcarbonyl, heterocyclylcarbonyl, (C₁₋₆)alkylene and (C₂₋₆)alkenylene; and the wavy line denotes either the E- or Z-isomeric position.

2. A compound according to claim 1, which is represented by the formula (IIA):

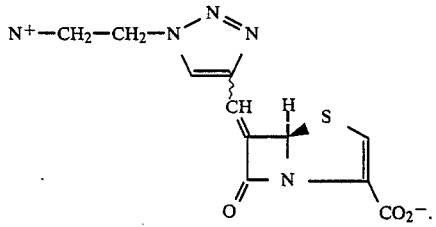

(IIA)

3. A compound according to claim 1, wherein the nitrogen-containing heterocyclyl group is aromatic.

4. A compound according to claim 3, wherein the nitrogen containing heterocyclyl group is an unsubstituted or substituted pyrid-1-yl group.

5. A compound according to claim 1, which is selected from the following compounds:

(5R)-(Z)-6-[1-(2-pyridinioethyl)-1,2,3-triazol-4-ylmethylene)penem-3-carboxylate, (5R)-(Z)-6-(1-[2-(3-ethylpyridinio)ethyl]-1,2,3-triazol-4-ylmethylene)penem-3-carboxylate, (5R)-(Z)-6-(1-[2-(4-methylpyridinio)ethyl]-1,2,3-triazol-4-ylmethylene)penem-3-carboxylate, (5R)-(Z)-6-(1-[2-(2-methylpyridinio)ethyl]-1,2,3-triazol-4-ylmethylene)penem-3-carboxylate, (5R)-(Z)-6-(1-[2-(4-cyclopropylpyridinio)ethyl]-1,2,3-triazol-4-ylmethylene)penem-3-carboxylate, (5R)-(Z)-6-(1-[2-(2,3-cyclopentenopyridinio)ethyl]-1,2,3-triazol-4-ylmethylene)penem-3-carboxylate, (5R)-(Z)-6-(1-[2-(4-phenylpyridinio)ethyl]-1,2,3-triazol-4-ylmethylene)penem-3-carboxylate, (5R)-(Z)-6-(1-[2-(3-hydroxymethylpyridinio)ethyl]-1,2,3-triazol-4-ylmethylene)penem-3-carboxylate, and (5R)-(Z)-6-[1-(2-pyridinioethyl)-1,2,3-triazol-4-ylmethylene)penem-3-carboxylate hemihydrate.

6. A pharmaceutically composition acceptable for treating bacterial injections comprising a compound according to claim 1, in admixture or conjunction with a pharmaceutically acceptable carrier.

7. A pharmaceutically acceptable composition according to claim 6, which additionally comprises a penicillin, cephalosporin or other β-lactam antibiotic.

8. A method of treating bacterial infection, which comprises administering to a human or animal in need thereof an antibacterially effective amount or a β-lactamase inhibitory amount of a compound of general formula (II) as defined in claim 1.

9. A method according to claim 8, wherein said compound is administered to said human or animal in conjunction with the prior, simultaneous or subsequent administration of a penicillin, cephalosporin, or other β-lactam antibiotic.

* * * * *

UNITED STATES PATENT AND TRADEMARK OFFICE
CERTIFICATE OF CORRECTION

PATENT NO. : 4,931,434
DATED : June 5, 1990
INVENTOR(S) : Nigel J.P. Broom et al It is certified that error appears in the above—identified patent and that said Letters Patent is hereby corrected as shown below:

Claim 1, column 12, line 57, "aryl($C_{-6}$)alkyl" should be -- aryl($C_{1-6}$)alkyl -- ;

Claim 6, column 14, line 13, "injections" should be -- infections -- .

Signed and Sealed this

Sixth Day of August, 1991

*Attest:*

HARRY F. MANBECK, JR.

*Attesting Officer*   Commissioner of Patents and Trademarks